US007338940B2

(12) United States Patent
Lampidis et al.

(10) Patent No.: US 7,338,940 B2
(45) Date of Patent: Mar. 4, 2008

(54) CANCER TREATMENT INCLUDING GLYCOLYTIC INHIBITORS

(76) Inventors: Theodore J. Lampidis, 6995 SW. 67th Ave., Miami, FL (US) 33143; Waldemare Priebe, 4239 Emory, Houston, TX (US) 77005

( * ) Notice: Subject to any disclaimer, the term of this patent is extended or adjusted under 35 U.S.C. 154(b) by 0 days.

(21) Appl. No.: 11/229,167

(22) Filed: Sep. 16, 2005

(65) Prior Publication Data
US 2006/0025351 A1 Feb. 2, 2006

Related U.S. Application Data

(62) Division of application No. 10/953,088, filed on Sep. 29, 2004, which is a division of application No. 10/401,457, filed on Mar. 28, 2003, now Pat. No. 7,160,865, which is a division of application No. 09/561,720, filed on May 1, 2000, now Pat. No. 6,670,330.

(51) Int. Cl.
A61K 31/7004 (2006.01)
(52) U.S. Cl. .......................................... 514/23; 424/649
(58) Field of Classification Search ................ 514/23; 424/649
See application file for complete search history.

(56) References Cited

U.S. PATENT DOCUMENTS

| | | | |
|---|---|---|---|
| 4,315,001 A | | 2/1982 | Blough |
| 4,420,489 A | * | 12/1983 | Whistler ................ 514/432 |
| 4,683,222 A | | 7/1987 | Stadler et al. |
| 4,684,627 A | | 8/1987 | LeVeen et al. |
| 4,840,939 A | | 6/1989 | Leveen et al. |
| 4,859,590 A | * | 8/1989 | Thiem et al. .................. 435/97 |
| 5,068,186 A | | 11/1991 | Schlingmann et al. |
| 5,077,034 A | * | 12/1991 | Kassis et al. ............... 424/1.73 |
| 5,185,325 A | | 2/1993 | Brawn et al. |
| 5,534,542 A | * | 7/1996 | O'Halloran et al. ......... 514/492 |
| 5,565,434 A | | 10/1996 | Barfknecht et al. |
| 5,643,883 A | | 7/1997 | Marchase et al. |
| 5,759,837 A | | 6/1998 | Kuhajda et al. |
| 5,977,327 A | | 11/1999 | Dziewiszek et al. |
| 6,218,435 B1 | | 4/2001 | Henry et al. |
| 6,319,695 B1 | | 11/2001 | Wong et al. |
| 6,489,302 B1 | | 12/2002 | Wiessler et al. |
| 2002/0035071 A1 | | 3/2002 | Pitha et al. |
| 2002/0077300 A1 | | 6/2002 | Kholsa et al. |
| 2003/0072814 A1 | | 4/2003 | Mailbach et al. |
| 2003/0087961 A1 | | 5/2003 | Ko et al. |

FOREIGN PATENT DOCUMENTS

| | | |
|---|---|---|
| EP | 0565785 A1 | 10/1993 |
| GR | 980100107 | 11/1999 |
| JP | 54041384 | 4/1979 |
| WO | 01/82926 A1 | 11/2001 |
| WO | WO 02/058741 A2 | 8/2002 |
| WO | WO 2006-020403 | 2/2006 |
| WO | WO 2006/020403 | 2/2006 |

OTHER PUBLICATIONS

Bessell, E. et al "Some in vivo and in vitro antitumor effects . . ." Eur. J. Cancer (1973) vol. 9, pp. 463-470.*
Bessell, E. et al "The use of deoxyfluoro-D-glucopyranoses . . ." Biochem. J. (1972) vol. 128, pp. 199-204.*
Mohanti, B. et al "Improving cancer radiotherapy . . ." Int. J. Rad. Oncol. Biol. Phys. (1996) vol. 35, No. 1, pp. 103-111.*
Belfi, C. et al "Increased sensitivity of human colon cancer cells . . ." BBRC (1999) vol. 257, pp. 361-368.*
Yun, J. et al "Glucose-regulated stresses confer resistance to VP-16 . . ." Oncol. Res. (1995) vol. 7, pp. 583-590.*
Vivi, A. et al "Comparison of action of te anti-neoplastic drug Ionidamine . . ." Breast Cancer Res. Treat. (1997) vol. 43, pp. 15-25.*
Haga, N. et al "2-deoxyglucose inhibits chemotherapeutic drug-induced apoptosis . . ." Int. J. Cancer (1998) vol. 76 pp. 86-90.*
Saydijari, R. et al "2-deoxy-D-glucose inhibits the antitumor effects . . ." Invest. New Drugs (1989) vol. 7, pp. 131-138.*
Harrigan, P. et al. "Potentiation of hyperthermia . . ." Int. J. Hypertherm. (1972) vol. 8, pp. 475-483.*
Yamada, M."Cellular sensitization of cisplatin and carboplatin . . ." Cancer Chemother. Pharmacol. (1999) vol. 44, pp. 59-64.*
Jain, V. et al "Effects of 2-deoxy-D-glucose on glycolysis . . ." Int. J. Radiation Biol. Phys. (1985) vol. 11, pp. 943-950.*
Kaplan, O. et al "Effects of 2-deoxyglucose on drug-sensitive . . ." Cancer Res. (1990) vol. 50, pp. 544-551.*
Jones, D. et al "Monitoring of neoadjuvant therapy . . ." J. Nucl. Med. (1996) vol. 37, No. 9, pp. 1438-1444.*
Bassa, P. et al "Evaluation of preoperative chemotherapy . . ." J. Nucl. Med. (1996) vol. 37, No. 6, pp. 931-938.*
Findlay, M. et al "Noninvasive monitoring of tumor metabolism . . ." J. Clin. Oncol. (1996) vol. 14, No. 3, pp. 700-708.*
Sidky,Y. et al "Inhibition of angiogenesis by interferons . . ." Cancer Res. (1987) vol. 47, pp. 5155-5161.*
Kirsch, M. et al "Angiostatin suppresses malignat glioma . . ." Cancer Res. (1998) vol. 58, pp. 4654-4659.*

(Continued)

Primary Examiner—Leigh C. Maier
(74) Attorney, Agent, or Firm—Notaro & Michalos PC

(57) ABSTRACT

Glycolytic inhibitors are useful in the treatment of solid tumors by attacking anaerobic cells at the center on the tumor. 2-deoxyglucose, oxamate and various analogs thereof are identified as having a natural selective toxicity toward anaerobic cells, and will significantly increase the efficacy of standard cancer chemotherapeutic and radiation regiments as well as new protocols emerging with anti-angiogenic agents.

7 Claims, No Drawings

OTHER PUBLICATIONS

Urabe, T. et al "Clinical pilot study of intrahepatic arterial chemotherapy . . ." Oncology (1998) vol. 55, No. 1, pp. 39-47.*
Elias, A. et al "Dose escalation of the hypoxic cell sensitizer . . ." Clin. Cancer Res. (1998) vol. 4, pp. 1443-1449.*
E. M. Bessell et al., Some In Vivo and In Vitro Antitumor Effects of the Deoxyfluoro-D-Glucopyranoses, Europ. J. Cancer, 1973,463-470, vol. 9, Pergamon Press, Great Britian.
Jae Ho Kim et al., 5- Thio-D-Glucose Selectively Potentiates Hyperthermic Killing of Hypoxic Tumor Cells, Science, Apr. 14, 1978. 206-207, vol. 200.
Beverly A. Teicher et al Classification of Antineoplastic Agents by their Selective Toxicites toward Oxygenated and Hypoxic Tumor Cells, Cancer Research, Jan. 1981, 73-81, vol. 41.
Kiyofumi Yamanishi, Effects of Valinomycin on Hexose Transport and Cellular ATP Pools in Mouse Fibroblasts, Journal of Cellular Physiology, 1984, 163-171, vol. 119.
J. Shen et al., Coinduction of glucose-regulated proteins and doxorubicin resistance in Chinese hamster cells, Proc. Natl. Acad. Sci. USA, May 1987, 3278-3282, vol. 84, USA.
Christine S. Hughes et al., Resistance to Etoposide Induced by Three Glucose-regulated Stresses in Chinese Hamster Ovary Cells, Cancer Research, Aug. 15, 1989.4452-4454. vol. 49.
Peter Buhl Jensen et al., Doxorubicin sensitivity pattern in a panel of small-cell lung-cancer cell lines: correlation to etoposide and vincristine sensitivity and inverse correlation to carmustine sensitivitv, Cancer Chemotherapy and Pharmacology. 1992.
Jisoo Yun et al., Glucose-regulated Stresses Confer Resistance to VP-16 in Human Cancer Cells through a Decreased Expression of DNA Toppoisomerase II, Oncology Research. 1995.583-590. vol. 7. Pergamon Press. USA.
Akihiro Tomida et al., Glucose-Regulated Stresses Induce Resistance to Camptothecin in Human Cancer Cells, Int. J. Cancer, 1996,391-396, vol. 68 International Union Against Cancer.
J. R. Colofiore et al., Enhanced Survival of Adriamycin-treated Chinese Hamster Cells by 2-Deoxy-D-glucose and 2,4-Dinitrophenol, Cancer Research, Oct. 1982, 3934-3940, vol. 42.
Karczmar, et al., Cancer Res., Jan. 1, 1992, 52:71-6.
Juling-Pohlit et al., Strahlenther. Onkol., 1990, 166(1):6-9.
Saydjari et al., Invest. New Drugs, 1989, 7:131-8.
Mack et al., Eur J Cancer Clin. Oncol., Sep. 1988, 24(9):1433-7.
Kern et al., Surgery, Aug. 1987, 102(2):380-5.
Gridley et al., Int. J. Rad. Oncol. Biol. Phys., Mar. 1985, 11:567-74.
Dills et al., J. Nutr., 1984, 114(11):2097-106.
Tannock et al., Cancer Res., Mar. 1983, 43(3):980-3.
Bernal et al., Science, Oct. 14, 1983, 222:169-72.
Purohit, Int. J. Rad. Oncol. Biol. Phys., Mar.-Apr. 1982, 8(3-4):495-9.
Laszlo et al., JNCI, Feb. 1960, 24 (2):267-279.
Ball et al., Cancer Res., Apr. 1957, 17(3):235-9.
Sokoloff, et al., AMA Arch. Path., Jun. 1955, 59(6):729-32.
Woodward et al., "2-desoxy-D-glucose as an inhbitor of anaerobic glycolysis in tumor tissue", Notes Biochem. Res. Found., Journal of the Franklin Institute, vol. 254, issue 3, pp. 259-260, Sep. 1952.
Abbink et al., J. Card. Pharml., 2001, 37:94-100.
Adler et al., Neuropsychopharmacology, 2000, 22(5):545-50.
George et al., Alcohol Clin. Exp. Res., May/Jun. 1994, 18(3):685-91.
Breier et al., Arch. Gen. Psychiatry, Jul. 1993, 50:541-50.
Breier et al., Psychopharmacology, 1991, 104:479-84.
Breier et al., Biol. Psychiatry, 1989, 26:438-62.
Fagius et al., Am. J. Physiol., 1989, 256(6.1):E714-20.
Hansen et al., Ped. Res., 1984, 18(5):490-5.
Hansen et al., Metabolism, Oct. 1983, 32(10):960-70.
Kerr et al., Metabolism, Oct. 1983, 32(10):951-9.
Thompson et al., Metabolism, Oct. 1981, 30(10):1015-20.
Thompson et al., Am. J. Physiol., Sep. 1980, 239(3):291-295.
Thompson et al., Science, Dec. 9, 1977, 198:1065-8.
Woolf et al., J. Clin. Endocr. Metab., 1977, 45(3):377-83.
Weber et al., J. Surg. Res., 1975, 18:491-5.
Burckhardt et al., Digestion, 1975, 12;1-8.
Gough et al., Gut, 1975, 16:171-6.
Brodows et al., J. Clin. Invest., Aug. 1973, 52:1841-4.
Sizonenko et al., Ped. Res., 1973, 7:983-93.
Peytremann et al., Europ. J. Clin. Invest., 1972,2:432-8.
Freinkel et al., NEJM, Oct. 26, 1972, 287(17):841-5.
Lipman et al., Metabolism, 1970, 19(11)980-7.
Thomas et al., Gut, 1968, 28:535-42.
Grasso et al., J.Clin. Endocr., 1968, 28:535-42.
Wegienka et al., Metabolism, Mar. 1967, 16(3):245-56.
Wegnieka et al., J. Clin. Endocr., Jan. 1966, 26:37-45.
Duke et al., Lancet, Oct. 30, 1965, 871-6.
Harlan et al., J. Clin. Endocrinol. Metab., Jan. 1963, 23:41-9.
Laszlo et al., J. Clin. Invest., Jan. 1961, 40:171-6.
Landau et al., JNCI; Sep. 1958, 21(3):485-494.
Mohanti et al., Int. J. Rad. Oncol. Biol. Phys., 1996, 35(1):103-11.
Blough et al., JAMA, Jun. 29, 1979, 241(26): 2798-2801.
Song et al., Cancer Res., Dec. 1978, 38:4499-4503.
Song et al., Br. J. Cancer, 1978, Suppl. III:136-140.
Song et al., JNCI, Sep. 1976, 57(3):603-605.
Clavo et al., J. Nuc. Med., Sep. 1995, 26(9):1625-1632.
Mesmer et al., Biochem. Mol. Biol. Int., Oct. 1996, 40(2):217-33.
Liu et al., Biochem. Pharmacol., 2002, 64:1745-51.
AFT et al., Br. J. Cancer, 2002,87:805-12.
Chandna et al., Rad. Res., 2002, 157:516-25.
Mese et al., Anticancer Res., 2001,21:1029-33.
Liu et al., Biochemistry, May 8, 2001, 40:5542-7.
Reinhold et al., Oncol. Rep., 2000, 7:1093-97.
Yamada et al., Cancer Chemother. Pharmacol., 1999, 44:59-64.
Dwarakanath et al., Int. J. Rad. Oncol. Biol. Phys., 1999.
Belfi et al., BBRC, 1999, 257:361-8.
Kalia, Indian J. Med Res., May 1999, 109:182-7.
Haga et al., Int. J. Cancer, 1998, 76:86-90.
Malaisse et al., Cancer Lett., Mar. 13, 1998, 125(1-2):45-9.
Chatterjee et al., Cancer Res., Nov. 15, 1997, 57:5112-16.
Kaplan et al., Cancer Res., Apr. 15, 1997, 57:1452-9.
Vivi et al., Breast Cancer Res. Treat., 1997, 43:15-25.
Tomida et al., Oncogene, 1996, 13:2699-2705.
Kraegen et al., Am. J. Physiol., 1985, 248:E353-E362.
Yun et al., Oncology Res., 1995, 7(12):583-590.
Halika et al., Cancer Res., Jan. 15, 1995, 55:444-9.
Schaider et al., J. Cancer Res. Clin. Oncol., 1995, 1121(4):203-10.
Griffiths et al., Int. J. Biochem., 1993, 25(12):1749-55.
Kalia et al., Indian J. Exp. Biol., Apr. 1993, 25(12):1749-55.
JHA et al., Int. J. Rad. Biol., 1993, 63(4):459-67.
Haberkorn et al., J. Nucl. Med., Nov. 1992, 33(11):1981-7.
Cay et al., Cancer Res., Oct. 15, 1992, 52:5794-6.
Kaplan et al., Cancer Res., Oct. 15, 1992, 52:5794-6.
Kaplan et al., Cancer Res., Feb. 1, 1990, 50:544-51.
Dwarakanath et al., Indian J. Med. Res., Jun. 1990, 92:183-8.
Ohtani et al., Jpn. J. Exp. Med., Apr. 1990, 60(2):57-65.
Herr et al., Cancer Res., Apr. 15, 1988, 48:2061-3.
Jain et al., Int. J. Radiant. Oncol. Biol. Phys., May 1985, 11(5):943-50.
Lampidis et al., Cancer Res., Feb. 1983, 43:716-20.
Steiner et al., Cancer Lett., Jul. 1983, 19(3):333-42.
Sridhar et al., Br. J. Cancer, 1978, 37:141-4.
Myers et al., BBRC, 1975, 63(1):164-71.
Bessel et al., Biochem. J., 1972, 128:199-204.
Bicz et al., Arch. Immunol. Ther. Exp., 1967, 15(1):112-4.
AFT et al., Proceed, AACR, Mar. 2003, 44: Abstract No. 123.
Richardson et al., Proceed, AACR, Mar. 2003, 44: Abstract No. 6239.
Wan et al., FASEB J., Jun. 2003, 17(9):1133-4 (Web version).
Dwarkakanath et al., Indian J. Exp. Biol., Sep. 1999, 37(9):865-70.
Latz et al., Strahlenther. Onkol., 1993, 169(7):405-11.
Harrigan et al., Int. J. Hyperthermia, 1992, 8(4):475-83.
Kerr et al., abstract entitled "Normal production and increased oxidation of glucose associated with epinephrine defiency in keotoic hypoglycemia", Pediatric Research, 8:434, 1972.
Zhang, L. et al "combined anti-fetal liver kinase 1 . . ." Cancer res. (2002) vol. 62, pp. 2034-2042. cited by examiner.
Weglenka et al., abstract entitled "Use of 2-deoxy-D-glucose to stimulate function of adrenal medulla", Clinical Res., vol. XIII, No. 1, pp. 134, Jan. 1965.

Wing Lam et al., Synergism of energy starvation and dextan-conjugated doxorubicin in the killing of multidrug KB carcinoma cells, Anti Cancer Drugs, 1999, 171-178, vol. 10, cited by other.

Görlach et al., Changes in growth, pO2 and pH after exposure to oxamate: studies of two human tumour cell lines growing as multicellular spheroids, International Journal of Oncology 7: p. 831-839, 1995.

Porter et al., The Renal Toxicity of (R) -3-Chlorolactate in the Rat, Chem-Biol Interactions, 62(1987) p. 157-166 Elsevier Scientific Publishers Ireland Ltd.

Izzedine et al., Antiviral Drug- Induced Nephrotoxicity, American Journal of Kidney Diseases, vol. 45, No. 5 May 2005 p. 804-817.

Jones et al., Renal and Spermatozoal Toxicity of—Bromohydrin, 3-Bromolactate and 3-Bromopyruvate, Journal of Applied Toxicology, vol. 16 (1), p. 57-63 (1996).

Ko et al., Glucose catabolism in the rabbit VX2 Tumor model for liver cancer: characterization and targeting hexokinase, Caner letters 173, 2001, p. 83-91 Elsevier Science Ireland Ltd.

Lü et al., Penicillamine: Pharmacokinetics and Differential Effects on Zinc and Copper Status in Chicks, Nutrient Metabolism, 1992 American Institute of Nutrition.

Papaconstantinou et al., The role of Glycolysis in the Growth of Tumor Cells, The Journal of Biological Chemistry vol. 236, No. 2, Feb. 1961, USA.

\* cited by examiner

CANCER TREATMENT INCLUDING GLYCOLYTIC INHIBITORS

CROSS-REFERENCE TO RELATED APPLICATIONS

This is a divisional of application Ser. No. 10/953,088 filed Sep. 29, 2004 which was a divisional of application Ser. No. 10/401,457 filed Mar. 28, 2003 now U.S. Pat. No. 7,160,865, which was a divisional of application Ser. No. 09/561,720 filed May 1, 2000, now U.S. Pat. No. 6,670,330, which are herein incorporated by reference.

STATEMENT OF GOVERNMENT INTEREST

The United States Federal Government may have certain rights with regard to this invention under NIH grant CA-37109-10.

FIELD AND BACKGROUND OF THE INVENTION

The present invention relates, in general, to compositions and methods aimed at effectively treating anaerobic tumor cells with inhibitors of glycolysis. It also extends to novel and useful methods and compositions for treating aerobic tumor cells with inhibitors of oxidative phosphorylation in combination with glycolytic inhibitors. Inhibiting oxidative phosphorylation to convert aerobic tumor cells to anaerobic cells, hypersensitizes them to glycolytic inhibitors.

U.S. patents that are relevant to the compositions and methods of the present invention are: U.S. Pat. Nos. 4,840,939 and 4,684,627, both for a treatment of cancer with phlorizin and its derivatives; U.S. Pat. No. 4,683,222 for N-glycosylated carboxamide derivatives and their use for influencing the body's inherent defenses; and U.S. Pat. No. 4,420,489 for sugars with sulfur replacing the ring oxygen atom as antiradiation agents. U.S. Pat. No. 4,840,939 is also relevant for its discussion of the work of Warburg in 1931, concerning the way cancer cells metabolize glucose.

Cancer cells at the inner core of a tumor are poorly oxygenated and consequently relyon anaerobic metabolism for survival. In this condition tumor cells divide more slowly than outer growing aerobic cells and consequently are more resistant to standard chemotherapeutic agents which target rapidly dividing cells. Thus, cells growing anaerobically in these instances exhibit a form of multidrug resistance (MDR) which contributes to chemotherapy failures in the treatment of solid tumors. Anaerobiosis, however, also provides a natural window of selectivity for agents that interfere with glycolysis.

This realization forms the basis for the present invention. According to the present invention, new opportunities are provided for increasing the efficacy of chemotherapeutic protocols. With data and knowledge accumulated by us in our previous work on mitochondrial agents, and with additional work performed by us now, various hypotheses have been formulated and verified to prove the efficacy of the present invention with regard to its compositions and its methods.

See, for example, a series of papers coauthored by one of the present inventors: Lampidis, T J, Bernal, S D, Summerhayes, I C, and Chen, L B. "Rhodamine 123 is selectively toxic and preferentially retained in carcinoma cells in vitro." NY Acad. Sci. 397:299-302, 1982; Summerhayes, I C, Lampidis, T J, Bernal, S D, Shepherd, E L, and Chen, L B. "Unusual retention of Rhodamine 123 by mitochondria in muscle and carcinoma cells." Proc. Natl. Acad. Sci. USA 79:5292-5296, 1982; Bernal, S B, Lampidis, T J, Summerhayes, I C, and Chen, L B. "Rhodamine 123 selectively reduces clonogenic ability of carcinoma cells in vitro." Science. 218:1117-1119, 1982; Lampidis, T J, Bernal, S D, Summerhayes, I C, and Chen, L B. "Selective toxicity of Rhodamine 123 in carcinoma cells in vitro." Cancer Res. 43:716-720, 1983; and Bernal, S B, Lampidis, T J, Mclsaac, B, and Chen, L B. "Anticarcinoma activity in vivo of Rhodamine 123, a mitochondrial-specific dye." Science. 222:169-172, 1983; which showed that Rhodamine 123 (Rho 123) which localizes in mitochondria of living cells, and uncouples ATP synthesis from electron transport, preferentially accumulates in, and kills, a variety of tumor cells as compared to a number of normal cells. We reasoned for the present invention that tumor cells treated with this drug would have to rely solely on glycolysis for ATP production and thus become hypersensitized to inhibitors of glycolysis, like 2-dg (2-dg). In contrast, mitochondrial function in normal cells remained unaffected when treated with Rho 123 and therefore these cells were not hypersensitive to 2-dg. In fact, we found that co-treating human breast carcinoma cells, MCF-7, with Rho 123 and 2-dg, at a dose of Rho 123 that alone inhibited 50% of colony forming units, and at a dose of 2-dg which produced no toxicity, 100% of the colony forming units was inhibited.

This concept was carried over to in vivo studies in which it was found that animals with implanted tumors that were treated in combination with 2-dg and Rho 123 were cured whereas when treated with either drug alone, only partial or no responses were obtained. This latter result provides evidence that manipulation of Oxphos and glycolysis simultaneously can cure tumors in animals. Furthermore, this in vivo data also demonstrates that 2-deoxyglocose can be administered safely to animals, at doses which are effective for anti-tumor activity in combination with an Oxphos inhibitor. In this regard, several reports have shown that low levels of 2-dg can be safely administered to animals for various reasons including hypersensitization of tumors to irradiation.

SUMMARY OF THE INVENTION

The present invention is based on the discovery that glycolytic inhibitors and analogs thereof, are selectively toxic to tumor cells which are metabolizing anaerobically. Thus, in conjunction with standard chemotherapy and/or radiation which is focused on aerobic, fast-growing cells, which we will here refer to collectively and individually as "aerobic treatment", use of these inhibitors will add to the efficacy of cancer treatment by selectively killing the anaerobically slow-growing tumor cells found at the inner core of solid tumors which are usually the most resistant and consequently the most difficult to eradicate using aerobic treatments.

As an aid for explaining and for demonstrating the usefulness of the present invention, we refer to the equation (A)=(B)=(C) where:

(A)=tumor cells treated at a dose of rhodamine 123 which specifically uncouples ATP synthesis from electron transport;

(B)=$\rho^\circ$ cells which are cells that contain no mitochondrial DNA and therefore cannot undergo oxidative phosphorylation; and (C)=tumor cells which are growing anaerobically.

In all three classes, the cells can only produce ATP via the Embden-Myerhoff pathway (glycolysis) and thus are naturally hypersensitive to all inhibitors of glycolysis exemplified by 2-deoxyglucose, oxamate and novel compounds of the present invention.

Although Warburg originally proposed that tumor cells depend less on mitochondrial function for ATP production and more on glycolysis than normal cells, there has been no definitive data to date to confirm this hypothesis. There is data however which indicates that cells, tumor or normal, which are compromised aerobically and switch to anaerobic metabolism increase their uptake and utilization of glucose. The increased uptake has been attributed to the increased appearance of glucose receptors on the plasma membrane. The fact that cells growing at the inner core of tumors rely more on glycolysis than cells on the outer edge most likely accounts for the successful use of the radioactive analog of glucose, 2-deoxyglucose (2-dg), as a diagnostic tool for localizing tumors. This has been the main usage of 2-dg for cancer. Moreover, it has been suggested that 2-dg is taken up more by anaerobic cells due to enhanced expression of glucose receptors. Thus, since a cell that is functioning normally relies mainly on oxidative phosphorylation for its supply of ATP when this mechanism is compromised or absent, glycolysis (the only other way of producing ATP) automatically becomes enhanced. This is precisely why inner core tumor cells should naturally become hypersensitive to agents which block glycolysis, i.e. 2-dg and others that block the glycolytic pathway at different steps, such as oxamate and iodoacetate.

Oxamate is another agent which blocks glycolysis and is more specific than 2-dg for anaerobically metabolizing cells. Oxamate has been shown to inhibit lactic dehydrogenase, the enzyme which breaks down pyruvate to lactic acid. Thus, the fact that oxamate blocks glycolysis at a different step than 2-dg, and is clearly active in our in vitro cell systems in selectively killing anaerobic cells (models A and B), lends further proof that our discovery is correct and works according to the principles we set forth in this application. The enzyme reaction which converts pyruvate to lactate occurs only when the cell's ability to process oxygen becomes limited. Thus, aerobically metabolizing cells do not use this enzyme and inhibitors of this reaction will inherently be more selective than inhibitors of glycolysis such as 2-deoxyglucose since these latter agents inhibit reactions that occur in aerobic as well as anaerobic cells.

Iodoacetate, on the other hand, is known to inhibit glycolysis at another step in the pathway, namely at glyceraldehyde 3-phosphate dehydrogenase, which normally yields 1,3 biphosphoglycerate from glyceraldehyde 3-phosphate and requires NAD+ to proceed.

The inventors have investigated this overall concept by utilizing an osteosarcoma cell line that has been selected for loss of mtDNA, and thus cannot produce ATP by oxidative phosphorylation (cells (B) above). The inventors have also utilized this concept as a model to determine whether any test drug utilizes functional mitochondria as a cytotoxic target. The model indicates that a drug which interferes with ATP production in mitochondria of whole cells, but not necessarily in isolated mitochondrial preparations, will hypersensitize a cell to glycolytic inhibitors, i.e. 2-dg, oxamate and iodoacetate. Data has been developed by the inventors which clearly shows that in the cases listed as (A) and (B) above, both are hypersensitive to 2-deoxyglucose, oxamate and iodoacetate which forms the basis for the present invention.

The data which supports the invention that anaerobic cells within a tumor are selectively sensitive to glycolytic inhibitors, indicates that this is a universal phenomenon and that most or all glycolytic inhibitors will, in general, be similarly effective.

The various features of novelty which characterize the invention are pointed out with particularity in the claims annexed to and forming a part of this disclosure. For a better understanding of the invention, its operating advantages and specific objects attained by its uses, reference is made to the accompanying descriptive matter in which preferred embodiments of the invention are illustrated.

DESCRIPTION OF THE PREFERRED EMBODIMENTS

The present invention identifies classes of novel compositions and novel methods of using them, as well as novel methods of using classes of known compositions to kill anaerobic tumor cells and to enhance the effectiveness of aerobic treatments for killing aerobic tumor cells.

The inventors have identified six categories of glycolytic inhibitors that can be used according to the present invention.

1. Analogs that Increase Tumor Targeting and Uptake:

(a) Lipophilic analogs of 2-deoxy-D-glucose.

In order to increase the uptake of 2-deoxyglucose into the inner core of slow growing anaerobic cells, increases in lipophilicity aids in penetration and therefore higher levels reaching these inner cells. In part, such analogs might also work as lipophilic prodrugs of 2-deoxy-D-glucose.

Examples: Lipophilic analogs include derivatives of hydroxyl groups like esters, ethers, phosphoesters, etc. Others include the removal of the hydroxyl group and replacement with halogens like fluorine or iodine, or with thiol or thioalkyl groups.

(b) Liposome formulated 2-deoxy-glucose and its analogs (also inhibitors of glycolysis such as oxamate and iodoacetic acid). Due to the ability to change the lipophilic nature of the outer surface of liposomes and entrap drugs for better delivery to different tissue sites, liposomes have previously been shown to increase tumor uptake of a variety of different drugs and molecules in experimental tumor models.

(c) Enzymatically cleavable derivatives of 2-deoxyglucose.

Examples of this class of compounds include Glucoronides with glycosides at the C-1 position. The rationale of the invention is that the level of the enzyme glucoronidase has been shown to be higher in tumors than in normal tissues. Thus, by synthesizing 2-deoxyglucose in the form of a glucoronide its concentration at the tumor site will be naturally enhanced by the increased levels of glucoronidases which will cleave it and deliver active 2-deoxyglucose specifically to the tumor.

2. Analogs of D-hexopyranoses:

For this disclosure the word "hexopyranoses" is used to cover all configurational isomers of monosaccharides modified at C-6 by removal (replacement) of 6-OH or by blocking it.

Such analogs will not be transformed by hexokinase or glucokinase to glucose-6-phosphate and can potentially block both enzymes.

Examples: 6-deoxy-D-glucose, 6-fluoro-D-glucose, and 6-O-methyl-D-glucose.

3. Analogs Blocking Transformation from Glucose 6-phosphate to Fructose 6-phosphate:

(a) Such transformation requires the presence of an hydroxyl group at C-2. Therefore, analogs without hydroxyl or having the hydroxyl properly blocked easily undergo the first step of 6-O-phosphorylation by hexokinase or glucokinase but will not undergo isomerization by phosphoglucose isomerase. In fact such compounds can efficiently block the enzyme.

Examples: 2-deoxy-D-glucose itself and its analogs. Other useful analogs are 2-deoxy-2-halo-D-glucose, for example 2-fluoro- or 2-iodo-D-glucose.

(b) Another way to stop isomerization is modification at C-1. Replacement of hydroxyl by fluorine (glucosyl fluoride) or simple deoxygenation to 1-deoxy-D-glucose.

4. Analogs Blocking the Aldolase A Cleavage, Thus Blocking Formation of Trioses from Fructose 1,6-bisphosphate:

Such a process requires the presence of hydroxyl groups at C-3 and C-4. Thus, for example, 3-deoxy or 3-fluoro-D-glucose or 4-deoxy or 4-fluoro-D-glucose can be transformed to 4-fluoro-D-fructose 1,6-bisphosphate, which will not be cleaved by aldolase A but will block it.

5. Blocking any of the Transformations of Glyceraldehyde:

Alterations are made at any step where phosphorylation is involved. Here either 2-fluoro or 3-fluoro-glyceraldehydes or glycerates can be used. If the phosphoester is important for blocking the enzyme, then, for example, 3-fluoro-2-phosphoglycerate is used to block transformation to phosphoenolpyruvate Also, phosphothioesters or other phosphor modified analogs can block the transformations of glyceraldehyde.

6. The Pyruvate Structure:

Keeping in mind that oxamate is a good inhibitor of lactate dehydrogenase, compositions or structures of the present invention which are efficient blockers of lactate dehydrogenase are included. An example is 2-fluoro-propionic acid or it salts; 2,2-difluoro-propionic acid.

Other examples are a pyruvate modified at C-3 such as 3-halo-pyruvate; 3-halopropionic acid, 2-thiomethylacetic acid.

In addition to the proposed use of inhibitors of glycolysis as supplements to current chemotherapeutic and radiation treatment, the recent emergence of anti-angiogenic factors aimed at cutting off the blood supply to tumors and thus creating a more anaerobic environment, indicates that the present invention will likely have applicability to this newly developing cancer therapy as well;

General Synthesis of Novel Chemicals:

The following section discloses the synthesis of analogs of glycolytic intermediates and determines their toxic potencies in $\rho^\circ$ cells and in tumor cells pretreated with Oxphos inhibitors.

According to the invention, a series of compounds has been rationally designed and prepared, that can block various steps of the glycolytic pathway, and which thus have an effect on cell models A, B, and C.

It is commonly believed that the three irreversible reactions of glycolysis catalyzed by hexokinase, phospho-fructokinase, and pyruvate kinase are the controlling elements of this pathway. Thus, it would appear that the design and synthesis of inhibitors should focus on these steps. However, due to the complexity of interactions between glycolysis and other pathways it is likely that restricting the focus to the controlling elements is too naive. Thus, we will consider all reactions in the glycolytic pathway as potential targets and design compounds accordingly.

Specifically, we have designed and synthesized the following, noting that the number in parenthesis after each analog corresponds to the structure illustrated in the following pages Hexokinase Blockers.

6-Fluoro-D-glucose (1) and 6-thio-D-glucose (2) are synthesized. Removal of the hydroxyl group from the C-6 carbon in glucose and replacement with fluorine (6-fluoro-D-glucose) and replacement with a thiol group respectively. 6-fluoro-D-glucose should prevent formation of glucose 6-phosphate and inhibit hexokinase. 6-Thio-D-glucose (2) behaves similarly to 6-fluoro-D-glucose (1) or may be transformed into a 6-thiophosphate derivative. In either case, they effectively block glycolysis.

Analogs Blocking Transformation from Glucose 6-phosphate to Fructose 6-phosphate.

Transformation of glucose 6-phosphate to fructose 6-phosphate requires a hydroxyl group at C-2 in the glucose molecule. Therefore, analogs lacking a hydroxyl in this position, or having a properly blocked hydroxyl might easily undergo 6-O-phosphorylation by hexokinase but will not be able to undergo isomerization by phosphoglucose isomerase to fructose 6-phosphate. In fact, 2-dg is an example of such a glucose analog that efficiently stops glycolysis at the isomerization step. Other potentially useful C-2-modified analogs that can be prepared are 2-bromo-D-glucose, 2-fluoro-D-glucose, and 2-iodo-D-glucose (4-5).

In addition, it should be possible to stop isomerization via modification at C-1 or C-5. In the case of C-1, the hydroxyl at C-1 is replaced with fluorine glucosyl fluoride (7) or with hydrogen to produce 1-deoxy-D-glucose. In the case of C-5, sulfur replaces oxygen in the hexopyranose ring of glucose to obtain 5-thio-D-glucose (8).

Analogs Blocking Aldolase-catalyzed Cleavage.

In the next step of glycolysis, fructose-6-phosphate is transformed to fructose 1,6-biphosphate. Subsequently, fructose 1,6-biphosphate undergoes aldolase catalyzed cleavage to glyceraldehyde 3-phosphate and dihydroxyacetone phosphate. The cleavage reaction requires that fructose 1,6-biphosphate contains hydroxyl groups at positions C-3 and C-4. To exploit this requirement, we synthesize two glucose analogs modified with fluorine atoms at these positions, i.e. C-3 (3-fluoro-D-glucose)(9) and C-4 (4-fluoro-D-glucose)(10). These analogs are expected to undergo uninterrupted glycolysis to 3-fluor-fructose 1,6 biphsphate and 4-fluoro-, fructose 1,6-bisphosphate; however, neither of them should be able to undergo aldolase-catalyzed cleavage to trioses. Increased accumulation of such compounds should stop glycolysis at this step.

Analogs Blocking Glyceraldehyde 3-phosphate Transformation to Pyruvate.

Steps that occur later in the glycolytic pathway i.e. from glyceraldehyde 3-phosphate to pyruvate, are also targets for inhibitors of glycolysis. The transformation of glyceraldehyde 3-phosphate to 1,3-bisphosphoglycerate catalyzed by glyceraldehyde 3-phosphate dehydrogenase can be blocked by 1,1-difluoro-3-phosphate-glycerol (11) and 1,1-difluoro-glycerate (12) is synthesized. Furthermore, analogs modified at C-2 are prepared with the rationale that substitution at this position will affect the action of either one or all of the following enzymes, glyceraldehyde 3-phosphate dehydrogenase, phosphoglycerate kinase, and phosphoglyceromutase. Examples of these potential glycolytic blockers are 2-fluoro-, 2-iodo-, 2-thio-, or 2-methoxy-glyceraldehydes (13-16) or glycerates (17-20).

Considering the next step in the glycolytic pathway C-3-substituted trioses will have inhibitory properties by virtue of being able to block the catalyzed step. The analogs are 3-fluoro-, 3,3-difluoro-, enolase 3-iodo-, 3-carboxylo- and 3-thioglycerates (21-24).

Increasing the Lipophilicity of 2-dg

Lipophilic analogs of 2-dg act as prodrugs. Specifically, mono and diesters of 2-dg are designed for increased uptake in tumor cells. Such lipophilic esters enter the cell via passive diffusion instead of relying on glucose transporters and then are hydrolysed by esterases, leading to the release of 2-dg. Valerate, myristate, and palmitate are examples of lipophilic derivatives of 2-dg (26-37). Specifically useful are all four possible monoesters of 2-dg for each acid.

The structures of the inhibitors of the present invention are:

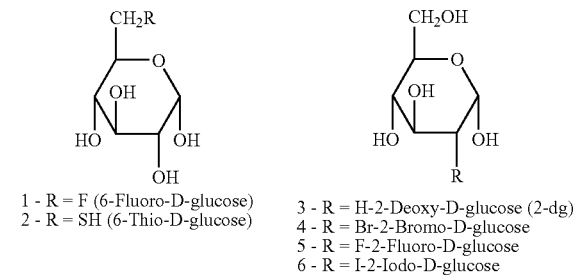

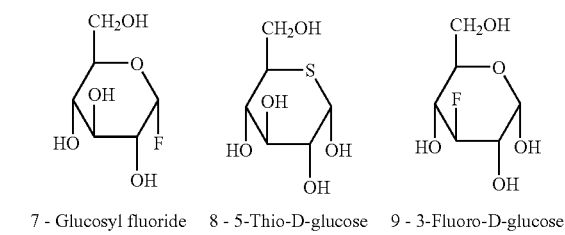

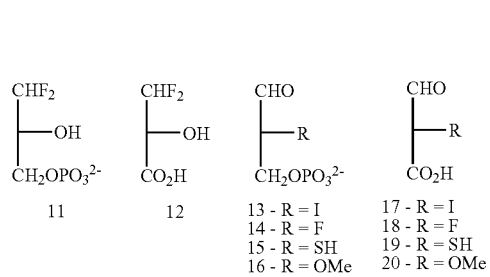

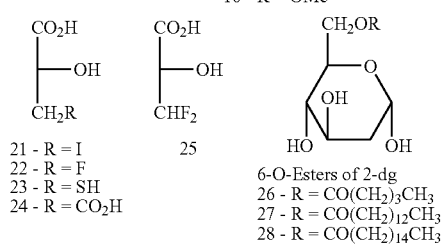

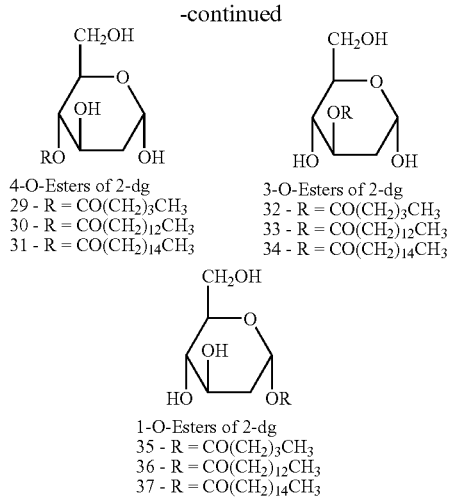

Diesters, however, are also useful. The pharmaco-kinetics of these mono and diester analogs of 2-dg, are different than that of the parent compound.

Test Results on Type (B) $\rho^o$ Cells.

When an osteosarcoma cell line (143B; Wild type in Table 1 below) was exposed for prolonged periods to ethidium bromide a mutant completely devoid of mitochondrial DNA $\rho^o$ was isolated. As a consequence this mutant cell line, referred to as either $\rho^o$ or cell line 206, cannot form intact respiratory chain complexes and therefore does not undergo electron transport and or oxidative phosphorylation. These processes are necessary for transmembrane proton pumping which creates an electronegative membrane potential ($\Delta\psi$mt) in the matrix side of the inner mitochondrial membrane. Since Rho 123 is a fluorescent dye, which due to its chemical positive charge accumulates in mitochondria, it is commonly used as an indicator of $\Delta\psi$mt. Thus, our results which show that the majority of $\rho^o$ cells stained dimly, while wt cells stained brightly after a 10 min. exposure to Rho 123, indicate that $\rho^o$ cells do indeed have an $\Delta\psi$mt, albeit reduced when compared to that in wt cells.

A mechanism by which $\rho^o$ cells are able to generate a $\Delta\psi$mt, has recently been proposed to occur via reversal of ATP transport into mitochondria through the adenine nucleotide transporter (ANT). Thus, by exchanging ADP for ATP, the internal environment of mitochondria becomes more electronegative. This process, however, does not appear to restore the $\Delta\psi$mt, to its normal value.

Flow cytometric analysis was performed in order to quantitate the differences observed microscopically between wild type 143B (wt) and $\rho^o$ cells (designated as cell line 206) in their accumulation of Rho 123. A four-fold decrease in Rho 123 retention in $\rho^o$ cells as compared to the parental wt has been observed. This data agrees with results from other investigators working with these same cells (Bochet and Godinet, and Barrientos and Moraes), in which they estimate that $\Delta\psi$mt of the $\rho^o$ cells to be 3-4 times lower than wt.

To ensure that our accumulation results were not complicated by P-gp-mediated MDR, since Rho 123 is a known substrate for this transporter, both cell types were examined for this gene by RT-PCR and were found not to express it. An interesting observation which may have significance for clinical application of Rho 123 and verapamil for detecting P-gp in freshly excised tumors or tumor samples from cancer patients is that in these non-P-gp cell lines, verapamil increases the retention of Rho 123.

The $\rho^\circ$ Cell Model as a Tool to Determine Whether Drugs Use Functional Mitochondria as a Cytotoxic Target.

Drugs which depend on functional mitochondria for localization, accumulation or for free radical formation, should be less potent in $\rho^\circ$ than in equivalent wt cells. Thus, it is not surprising to find that in growth inhibition studies, as shown in Table 1, $\rho^\circ$ cells are 50 and 6 times more resistant to Rho 123 and saffranin O (another mitochondrial cationic dye) than wt cells, respectively.

TABLE 1

| Drugs | 50% Growth Inhibition Dose (μg/ml) (CELLS) | | Ratio |
|---|---|---|---|
| | Wild type | $\rho^\circ$ | |
| Rhodamine 123 | 1.0 | 50 | 50 |
| Saffranin O | 0.35 | 2 | 6 |
| Doxorubicin | 0.01 | 0.01 | 1 |
| Vinblastine | 0.00075 | 0.00075 | 1 |
| Paclitaxel | 0.05 | 0.05 | 1 |
| 2-deoxy-glucose | 1000 | 50 | 0.05 |

The differences between wt and $\rho^\circ$ cells in their sensitivities to these mitochondrial localizing drugs appears to be due to the lack of functional mitochondria as a target, and the lowered $\Delta\psi$mt, in the $\rho^\circ$ cell, which leads to reduced accumulation of Rho 123 and Saffranin O in this latter cell type. Since Rho 123 acts as an uncoupler in isolated mitochondria, and it is dependent on the strength of both $\Delta\psi$mt, and plasma $\Delta\psi$ for intracellular accumulation, it is not surprising to find $\rho^\circ$ cells to be more resistant than wt cells to this drug. This, however, does not imply that Rho 123, or other mitochondrial localizing drugs kill the cell by inhibiting oxidative phosphorylation. It is not clear from our results whether a normally functioning cell with intact mitochondria will die if their mitochondria become uncoupled.

The fact that $\rho^\circ$ cells (cell model (B)) are able to grow without undergoing oxidative phosphorylation demonstrates that blockage of this process alone does not lead to cell death. It can be argued however, that $\rho^\circ$ cells have been selected to survive without oxidative phosphorylation capability and therefore have developed other mechanisms for this purpose. Thus, they are not equivalent to cells with normally functioning mitochondria that are treated with uncouplers (cell model (A)).

Nevertheless, the increased accumulation of the positively-charged drugs, Rho 123 and saffranin O, in wt vs $\rho^\circ$ cells, due to the increased $\Delta\psi$mt, in the former cell type, most likely contributes to their increased sensitivities to both drugs. In fact, as mentioned above, Bochet and Godinet, and Barrientos and Moraes, estimate that $\Delta\psi$mt, of these $\rho^\circ$ cells to be 3-4 times lower than wt which agrees with our results that show $\rho^\circ$ cells retain 4 times less Rho 123 than wt. Thus, by whatever mechanism Rho 123 ultimately kills a cell, the intracellular level of drug accumulation necessary for this action appears to be facilitated by the strength of the $\Delta\psi$mt However, the preliminary data we present with the cell model above, shows that when cells with normally functioning mitochondria, 143B or MCF-7, are co-treated with Rho 123 and glycolytic inhibitors, their survival is compromised. This clearly indicates that mitochondrial agents which inhibit Oxphos can hypersensitize tumor cells to glycolytic inhibitors and that this combinative effect is indeed the mechanism by which they inhibit cell growth and/or kill tumor cells.

In contrast, the nuclear localizing chemotherapeutic agent, Dox, is found to be equitoxic in both cell lines of cell model (B), indicating that functional mitochondria are not an important site for its cytotoxic action. Likewise, the tubulin-binding agents, paclitaxel and vinblastine are also found to be equitoxic in these cell lines. Moreover, as mentioned above with cell model (A), these drugs do not hypersensitize tumor cells to glycolytic inhibitors. Therefore, this data also acts as an important negative control to demonstrate that compounds which are not known to preferentially accumulate in mitochondria or interact with its function, do not hypersensitize tumor cells to glycolytic inhibitors. In fact, this data further indicates that both cell models (A) and (B) are specific in testing whether inhibition of Oxphos leads to hypersensitization to glycolytic inhibitors which results in growth inhibition and or cell death.

It should be noted here that the reason that $\rho^\circ$ cells do not display an MDR phenotype to the chemotherapeutic agents we have tested, even though they do not undergo Oxphos, is because they are growing rapidly in vitro. This is quite different from the in vivo situation where a cell in the middle of a tumor due to a number of reasons, is slow-growing and thus are resistant to most chemotherapeutic agents which target rapidly dividing cells. It is the hypoxic environment however that leads to the anaerobic metabolism these inner core tumor cells undergo, which makes them selectively sensitive to glycolytic inhibitors. This is the essence of our discovery.

As predicted, $\rho^\circ$ cells are more sensitive to 2-dg than wt cells showing an ID50 of 50 as compared to 1000 mg/ml for wt cells. Thus out of the six drugs presented in Table 1 above, 2-dg is the only one that $\rho^\circ$ cells are hypersensitive to. Preliminarily we have found similar differential sensitivity to oxamate and irdoacetate.

Thus, our data clearly support our working model that inhibition of Oxphos by either mitochondrial agents (cell model (A)) or by mutation in mitochondrial DNA, $\rho^\circ$ cells, (cell model (B)) renders both of them hypersensitive to glycolytic inhibitors. The third part of our equation, cell model (C), is at the center of our studies, in that tumor cells growing under hypoxic conditions are hypersensitive to inhibitors of glycolysis. The present invention, based on the differences and similarities of our three cell models should lead to a new approach to chemotherapy.

One of the problems with successful treatment of solid tumors is eradicating all of the tumor cells including those that are more centrally located. Due to their location, cancer cells at the inner core of the tumor are less oxygenated and therefor rely more on anaerobic metabolism in order to survive. In this condition they divide less rapidly than the more aerobic tumor cells and thus are more resistant to the standard chemotherapeutic agents which take advantage of rapidity of replication as a selective mode of toxicity. In addition, anaerobic cells are less able to produce free radicals when treated with chemotherapeutic agents or irradiation which utilize this part of the cell's capability in order to further potentiate its mode of action. Thus, anaerobiosis in these instances act as another component of resistance to successful chemotherapeutic and radiation treatment.

It should be noted that a gradient of anaerobiosis exists within tumors, therefor it is expected that the more anaerobic the cell becomes the more susceptible it becomes to glycolytic inhibitors, such as 2-deoxyglucose, oxamate and iodoacetate (the latter has been shown to block glycolysis at the glyceraldehyde 3-phosphate dehydrogenase step) and the analogs disclosed in this application. On the other hand, the more aerobic the cells become, the more sensitive they are to conventional chemotherapy and or radiation.

Therefore, we propose that glycolytic inhibitors, such as 2-deoxyglucose, oxamate, iodoacetate and the analogs we specify here, significantly increase the efficacy of standard cancer chemotherapeutic and radiation regimens as well as new protocols emerging with anti-angiogenic agents by selectively killing anaerobic tumor cells when given in combination with the above mentioned therapies.

Specifically, we have discovered that 2-dg or glycolytic inhibitors in general can be added to standard chemotherapy protocols that now exist for carcinomas and sarcomas, a few of which are listed below as representative examples, i.e.:

Breast cancer: Cytoxan (a trademark for cyclophosphamide, marketed by BMS), Adriamycin (a trademark for doxorubicin, marketed by Pharmacia), and 5FU, or Taxotere (a trademark for docetaxel, marketed by Aventis);

Sarcomas: Adriamycin I.V. and Cisplatin I.A. (intra arterial) or ifosphamide, Adriamycin and DTIC (all I.V.);

Lung cancer: Navelbine (a trademark for vinorelbine) and cisplatin or Taxotere and carboplatin or gemcitabine and cisplatin;

Small Cell Lung cancer: VP-16 and cisplatin;

Head and Neck cancer: 5FU and cisplatin;

Colon cancer: 5FU and leukovorin and CPT-11 (irinotecan); and

Multi-drug resistant (MDR) tumors: MDR tumors will be treated with a glycolytic inhibitor and drugs active against MDR tumors. Example: combination of 2-dg with Annamycin. Such combinations will be especially useful against breast cancer.

We also disclose treatment which combines blockers of oxphos with glycolytic inhibitors for general antitumor therapy. Treatment with the former agents will convert aerobic tumor cells to anaerobic, thus making them hypersensitive to glycolytic inhibitors. Blockage of Oxphos can be accomplished with agents that, in general, are positively-charged and are relatively lipophilic, examples of which are rhodamine 123, saffranin O, octylpyridium and others. In the case when tumor uptake is reduced by the presence of drug transporting proteins, such as P-gp or MRP (efflux proteins), this treatment will be used in combination with agents that block efflux, e.g. verapamil, cyclosporin.

Alternatively, lipophilic cationic compounds which inhibit oxidative phosphorylation in intact cells, but are not recognized by MDR transporting systems, such as alkylguanidinium analogs, can be used in the MDR+aerobic tumor cells to convert them to anaerobic cells and thereby render them hypersensitive to glycolytic inhibitors.

Moreover, glycolytic inhibitors are effective as single agent treatments for tumors which are mostly anaerobic and because of their size and location cause discomfort and blockage of normal function, i.e. head and neck tumors. These inhibitors are useful in reducing tumor size when administered orally, IV, IP or directly into the tumor.

Another application of the glycolytic inhibitors of the present invention is in the treatment of bacterial infections which involve anaerobes, such as clostridia, bacteriodes, etc.

Detail Syntheses of Novel Compounds:

Synthesis of the novel compounds can be achieved by those of ordinary skill in the art by understanding the following examples. Synthesis of 3,4,6-Tri-O-aceryl-D-glucal can be performed by the scheme:

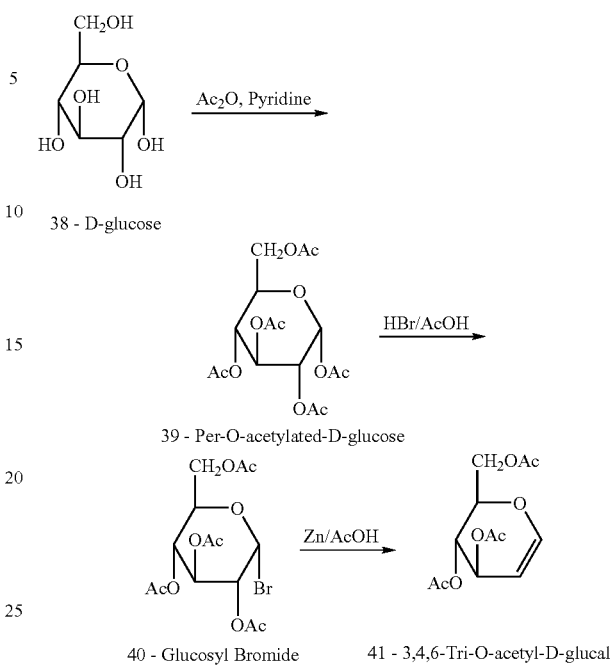

Compound 41 is then deacetylated to glucal 42, which is a key intermediate for the invention. First, it is deoxygenated at C-2 as 2-deoxy-glucose, but more importantly it contains hydroxyl groups that differ in their reactivity. This allows differentiation during blocking reactions and selective preparation of acylated derivative of D-glucal. Specifically, D-glucal 42 contains a primary hydroxyl at C-6 which is the most reactive in the molecule. Subsequently the secondary hydroxyl at C-3, because of its allylic position, is more reactive than the secondary hydroxyl at C-4.

Synthesis of D-glucal and its reactivity are illustrated by the following scheme:

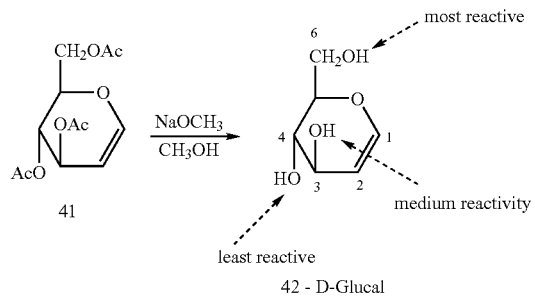

4-O-acylated derivative of 2-dg is prepared first. This is done by first blocking hydroxyls at C-6 and C-3, which will leave hydroxyl at C-4 open for acylation. The blocking groups at C-3 and C-6 should be selectively removed in the presence of esters. Such properties are demonstrated by silyl ethers, which are stable in basic but unstable in acidic conditions, whereas acyl groups appear to be stable in the latter conditions. Therefore, D-glucal 42 will first be silylated at C-3 and C-6 with sterically bulky t-butyldimethylchlorosilane (TBS) to 43 leaving a free hydroxyl at C-4 ready for the acylation with acyl chloride to 44 in the following scheme:

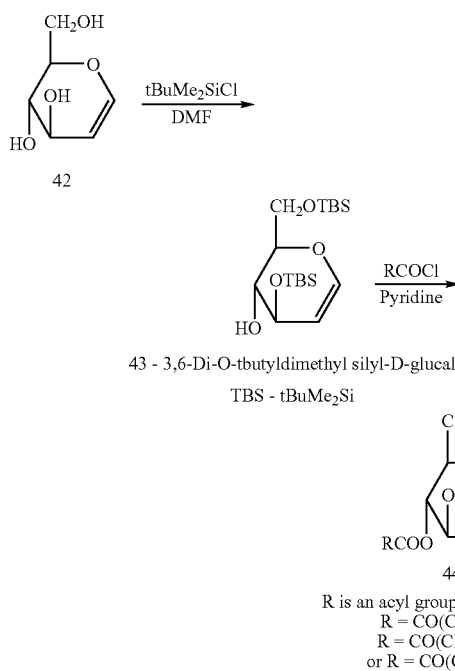

43 - 3,6-Di-O-tbutyldimethyl silyl-D-glucal

TBS - tBuMe₂Si

R is an acyl group as shown below
R = CO(CH₂)₃CH₃
R = CO(CH₂)₁₂CH₃
or R = CO(CH₂)₁₄CH₃

Compound 44 has a reactive double bond, which is reacted with silanol to substitute 2-deoxy-D-glucose 45 in the following scheme. This electrophilic addition reaction requires the presence of triphenylphospine hydrobromide. Compound 45 is then deprotected selectively at C-1, C-3 and C-6, yielding the desired 4-O-acylated analogs 29-31.

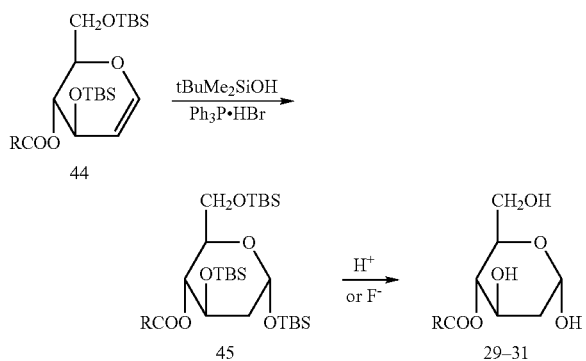

Using similar known strategies the other compounds of the invention can be prepared by those skilled in the art without undue experimentation, once the motivations to make these compounds, specifically the desire to make glycolytic inhibitors for the purpose of killing anaerobic cells, have been learned from the present disclosure.

The Novel Method:

Another aspect of the invention is a method of inhibiting one or more steps of the glycolytic pathway using an effective amount of one or more glycolytic inhibitors or schemes, in the presence of anaerobic cells, specifically for the purpose of thereby killing the cells. The disclosed compounds, used singly or in combination, have been shown to achieve this end. Other inhibitors and other inhibiting schemes may also be used, once the basic premises of the present invention are understood.

For example, known or new genetic manipulations to inhibit or block one or more steps in the glycolytic pathway may be used to practice the method of the invention.

For a better understanding of the pathway, and in particular the ten steps of the glycolytic pathway, any one or more of which may inspire the use of inhibitors or schemes to thwart for practicing the present invention, the pathway is set forth as follows:

| | Reactions of glycolysis | | | |
|---|---|---|---|---|
| Step | Reaction | | | |
| 1 | Glucose + ATP → glucose 6-phosphate + ADP + H⁺ | | | |
| 2 | Glucose 6-phosphate ⇌ fructose 6-phosphate | | | |
| 3 | Fructose 6-phosphate + ATP → fructose 1,6-bisphosphate + ADP + H⁺ | | | |
| 4 | Fructose 1,6-bisphosphate ⇌ dihydroxyacetone phosphate + glyceraldehyde 3-phosphate | | | |
| 5 | Dihydroxyacetone phosphate ⇌ glyceraldehyde 3-phosphate | | | |
| 6 | Glyceraldehyde 3-phosphate + $P_i$ + NAD⁺ ⇌ 1,3-bisphosphoglycerate + NADH + H⁺ | | | |
| 7 | 1,3-Bisphosphoglycerate + ADP ⇌ 3-phosphoglycerate + ATP | | | |
| 8 | 3-Phosphoglycerate ⇌ 2-phosphoglycerate | | | |
| 9 | 2-Phosphoglycerate ⇌ phosphoenolpyruvate + $H_2O$ | | | |
| 10 | Phosphoenolpyruvate + ADP + H⁺ → pyruvate + ATP | | | |
| Step | Enzyme | Type | $\Delta G^{OP}$ | $\Delta G$ |
| 1 | Hexokinase | a | −4.0 | −8.0 |
| 2 | Phosphoglucose isomerase | c | +0.4 | −0.6 |
| 3 | Phosphofructokinase | a | −3.4 | −5.3 |
| 4 | Aldolase | e | +5.7 | −0.3 |
| 5 | Triose phosphate isomerase | c | +1.8 | +0.6 |
| 6 | Glyceraldehyde 3-phosphate dehydrogenase | f | +1.5 | −0.4 |
| 7 | Phosphoglycerate kinase | a | −4.5 | +0.3 |
| 8 | Phosphoglycerate mutase | b | +1.1 | +0.2 |
| 9 | Enolase | d | +0.4 | −0.8 |
| 10 | Pyruvate kinase | a | −7.5 | −4.0 |

A Rapid Screening Method for Identifying Inhibitors of Oxidative Phosphorylation:

Lactate (more commonly known as lactic acid) is an end product of glycolysis that is activated when a cell cannot use oxygen as its final electron acceptor. This occurs when cells are metabolizing anaerobically. Thus, under these conditions, pyruvate, which is the last end product of glycolysis during aerobic metabolism, is further metabolized to lactate. We demonstrated that agents such as rhodamine 123 which inhibit oxidative phosphorylation in intact tumor cells (converting them from aerobic to anaerobic cells) hypersensitize them to inhibitors of glycolysis. This discovery created a need for a screening method to identify agents which inhibit oxidative phosphorylation and thereby render a cell hypersensitive to glycolytic inhibitors. Consequently, we have developed a rapid and an inexpensive way to detect such agents by measuring increases in the production of lactate in living cells.

We have found in our cell models A and B that measurement of the level of lactate correlates with the degree of anaerobiosis. It can be seen in the table below that in cell model B, ρo cells, which by nature of their deficiency in mitochondrial DNA cannot perform oxidative phosphorylation and are therefore metabolizing anaerobically, produce approximately 3 times more lactate (15.4 μg/μg protein) than their aerobic parental cell counterparts, 143b, (5.4 µg/µg protein). Similarly, in cell model A, (See table below) when the aerobically metabolizing cell, 143b, is treated with increasing doses of rhodamine 123, which should convert it to increasingly anaerobic growth, lactate is accordingly increased as a function of increasing rhodamine 123 doses. In contrast, chemotherapeutic drugs which affect aerobic cells such as Doxorubicin (Dox), Vinblastine (Vbl) and Taxol (a trademark for paclitaxel) and do not hypersensitize cells to glycolytic inhibitors, show little or no significant changes in lactate production. We thus provide convincing evidence that increase in lactate is reflective of increases in anaerobic metabolism which can be induced by agents which inhibit mitochondrial oxidative phosphorylation. Such methodology provides a practical means for testing and or screening extensive libraries of structurally diverse compounds to identify inhibitors of oxidative phosphorylation as well as for obtaining new leads to design novel inhibitors of this fundamental cellular process.

TABLE 2

LACTATE PRODUCTION IN CELL MODELS A & B

| CELL LINE | DRUG | DOSE (µg/ml) | LACTATE (µg/µg protein) |
|---|---|---|---|
| ρo | Control | 0 | 15.4 +/− 0.3 |
| 143b | Control | 0 | 5.4 +/− 0.1 |
| 143b | Rho 123 | 0.25 | 9.3 +/− 0.4 |
| 143b | Rho 123 | 0.50 | 13.2 +/− 0.2 |
| 143b | Rho 123 | 1.0 | 14.6 +/− 2.3 |
| 143b | Dox | 0.005 | 5.1 +/− 0.4 |
| 143b | Dox | 0.01 | 5.5 +/− 0.7 |
| 143b | Vbl | 0.0005 | 5.6 +/− 0.6 |
| 143b | Vbl | 0.001 | 6.3 +/− 0.9 |
| 143b | Vbl | 0.002 | 5.8 +/− 0.3 |
| 143b | Taxol | 0.0005 | 5.6 +/− 0.7 |
| 143b | Taxol | 0.0010 | 6.1 +/− 0.7 |
| 143b | Taxol | 0.0020 | 6.6 +/− 0.3 |

We have thus also demonstrated as part of this invention, that agents such as rhodamine 123 which inhibit oxidative phosphorylation in intact tumor cells, hypersensitize them to inhibitors of glycolysis by accelerating anaerobic metabolism.

Weight Loss Method:

Based on the principle of this discovery, we claim the extension of the use of this concept as a novel approach for weight control as follows:

Since anaerobic metabolizing cells take up and use glucose more rapidly than aerobic metabolizing cells, we propose to add small amounts of agents which localize in mitochondria and slow down oxidative phosphorylation. Thus, most cells in the body would have increased uptake and utilization of glucose, thereby lowering blood sugar levels. Under these conditions, in order to compensate for reduced glucose levels in the blood, gluconeogenesis would be increased by the liver. Gluconeogenesis is a process whereby glucose is synthesized by breakdown of fats. Thus, our treatment effectively increases the breakdown and utilization of stored fat. Currently, intense energetic exercise accomplishes the same thing most likely by a similar mechanism.

While specific embodiments of the invention have been shown and described in detail to illustrate the application of the principles of the invention, it will be understood that the invention may be embodied otherwise without departing from such principles.

What is claimed is:

1. A method of treating cancer in a human, said method comprising orally administering an effective amount of a pharmaceutical composition comprising 2-Deoxy-D-glucose in combination with a cancer chemotherapy protocol, subject to the limitation that said protocol does not include administration of an inhibitor of oxidative phosphorylation and further subject to the limitation that said administration is in the absence of radiation therapy.

2. A method of killing cancer cells in a human, wherein said cancer cells include cancer cells that create ATP for energy anaerobically and cancer cells that aerobically generate ATP, said method comprising administering a cancer chemotherapy protocol, said protocol not including administration of an inhibitor of oxidative phosphorylation in combination with orally administering a glycolvtic inhibitor capable of inhibiting at least one step of the glycolytic pathway, wherein said therapy is administered without radiation therapy, and said glycolytic inhibitor is of 2-Deoxy-D-glucose.

3. The method according to claim 2, wherein the at least one compound of the cancer chemotherapy protocol is selected from the group consisting of cyclophosphamide, doxorubicin, 5-fluorouracil, docetaxel, cisplatin, ifosphamide, DTIC, vinorelbine, carboplatin, gemoitabine, VP-16, leukovorin, an antiangiogenic agent, and irinotecan.

4. A method for treating a human with a carcinoma or sarcoma that contains both aerobically and anaerobically metabolizing cells, said method comprising the steps of:
  (a) administering a chemotherapy protocol, said protocol not including administration of an inhibitor of oxidative phosphorylation, for killing at least some of the aerobically metabolizing cells; and, in the absence of radiation therapy,
  (b) orally administering 2-Deoxy-D-glucose for killing at least some of the anaerobically metabolizing cells.

5. The method according to claim 4, wherein the chemotherapy protocol includes administering at least one of cyclophosphamide, doxorubicin, 5-fluorouracil, docetaxel, cisplatin, ifosphamide, DTIC, vinorelbine, carboplatin, gemcitabine, VP-16, leukovorin, an anti-angiogenic agent, and irinotecan.

6. A method for treating a human with a carcinoma or sarcoma that contains both aerobically and anaerobically metabolizing cells, said method comprising the steps of:
  (a) administering a chemotherapy protocol wherein the chemotherapy protocol includes administering an anti-angiogenic agent, and said protocol not including administration of an inhibitor of oxidative phosphorylation, for killing at least some of the aerobically metabolizing cells; and, in the absence of radiation therapy,
  (b) orally administering 2-Deoxy-D-glucose for killing at least some of the anaerobically metabolizing cells.

7. A method of killing cancer cells in a human, wherein said cancer cells include cancer cells that create ATP for energy anaerobically and cancer cells that aerobically generate ATP, said method comprising administering in the absence of radiation therapy, an anti-angiogenic agent in combination with orally administering a glycolytic inhibitor capable of inhibiting at least one step of the glycolytic pathway, wherein said glycolytic inhibitor is 2-Deoxy-D-glucaose.

* * * * *